United States Patent
Obler et al.

(10) Patent No.: US 11,717,251 B2
(45) Date of Patent: Aug. 8, 2023

(54) DETERMINING A COMPETENCY RELATIONSHIP, SETTING DOSE-RELATED RECORDING PARAMETER USING COMPETENCY RELATIONSHIP

(71) Applicant: Siemens Healthcare GmbH, Erlangen (DE)

(72) Inventors: Richard Obler, Erlangen (DE); Stanislav Tashenov, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 546 days.

(21) Appl. No.: 16/566,972

(22) Filed: Sep. 11, 2019

(65) Prior Publication Data
US 2020/0085402 A1   Mar. 19, 2020

(30) Foreign Application Priority Data
Sep. 19, 2018   (DE) .................. 10 2018 215 958.0

(51) Int. Cl.
*G16H 50/50*   (2018.01)
*A61B 6/00*   (2006.01)
(Continued)

(52) U.S. Cl.
CPC .............. *A61B 6/544* (2013.01); *A61B 6/463* (2013.01); *G16H 20/40* (2018.01); *G16H 30/20* (2018.01)

(58) Field of Classification Search
CPC .............................. G16H 30/20; G16H 50/50
(Continued)

(56) References Cited

U.S. PATENT DOCUMENTS

| 7,680,308 B2 * | 3/2010 | Dale | G16H 30/20 |
| | | | 382/128 |
| 10,552,959 B2 * | 2/2020 | Piron | A61B 5/7425 |

(Continued)

FOREIGN PATENT DOCUMENTS

| CN | 103654830 A | 3/2014 |
| CN | 104039262 A | 9/2014 |

(Continued)

OTHER PUBLICATIONS

Google patents search, Nov. 2, 2021 (Year: 2021).*

(Continued)

*Primary Examiner* — Dilek B Cobanoglu
(74) *Attorney, Agent, or Firm* — Lempia Summerfield Katz LLC

(57) ABSTRACT

A method for determining at least one competency relationship to be used as a basis for selection of a dose-related recording parameter for an examination process, in particular the recording of a timed series of x-ray images as an x-ray image dataset, of a patient at an x-ray device, between at least one competency value describing a user-specific or user-group specific user competency in respect of the evaluation of recorded x-ray images and at least the at least one recording parameter. The method includes displaying a plurality of x-ray image datasets corresponding to different recording parameters and/or having different image contents described by image content parameters; recording, for each x-ray image dataset, at least one measured value describing the competency value based on an interaction of a user with an operating device assigned to a display device; and determining, based on the measured values, the competency relationship describing the recording parameter-dependent competency value.

21 Claims, 4 Drawing Sheets

(51) Int. Cl.
  *G16H 30/20* (2018.01)
  *G16H 20/40* (2018.01)
(58) Field of Classification Search
  USPC .............................................. 382/128; 705/2
  See application file for complete search history.

(56) References Cited

U.S. PATENT DOCUMENTS

| | | | |
|---|---|---|---|
| 2007/0076842 A1 | 4/2007 | Tkaczyk et al. | |
| 2010/0203487 A1* | 8/2010 | Cyr .................... | G09B 23/286 434/262 |
| 2013/0077746 A1 | 3/2013 | Tsuji | |
| 2014/0050295 A1 | 2/2014 | Dennerlein et al. | |
| 2014/0079307 A1 | 3/2014 | Feuerlein et al. | |
| 2014/0088989 A1* | 3/2014 | Krishnapuram ....... | G16H 50/50 705/2 |
| 2014/0254748 A1 | 9/2014 | Funk | |
| 2014/0270053 A1 | 9/2014 | Larson | |
| 2015/0238160 A1 | 8/2015 | Flohr et al. | |
| 2015/0297916 A1* | 10/2015 | Chen ........................ | G06T 7/13 600/1 |
| 2016/0042499 A1 | 2/2016 | Dhanantwari et al. | |
| 2017/0079610 A1 | 3/2017 | Morf et al. | |
| 2017/0351937 A1 | 12/2017 | Lu | |
| 2018/0108128 A1 | 4/2018 | Schmidt | |

FOREIGN PATENT DOCUMENTS

| | | | |
|---|---|---|---|
| CN | 104573907 A * | 4/2015 | ....... G06Q 10/06398 |
| CN | 104856717 A | 8/2015 | |
| CN | 105144241 A | 12/2015 | |
| CN | 106550527 A | 3/2017 | |
| DE | 102016220093 A1 | 4/2018 | |
| EP | 3270178 A1 | 1/2018 | |

OTHER PUBLICATIONS

Ip.com search, Apr. 16, 2022 (Year: 2022).*
ACC/AHA Clinical Competence Statement, Circulation, Feb. 1, 2005, John W. Hirshfeld (Year: 2005).*
German Office Action for German Application No. 10 2018 215 958.0 dated Oct. 14, 2019.

* cited by examiner

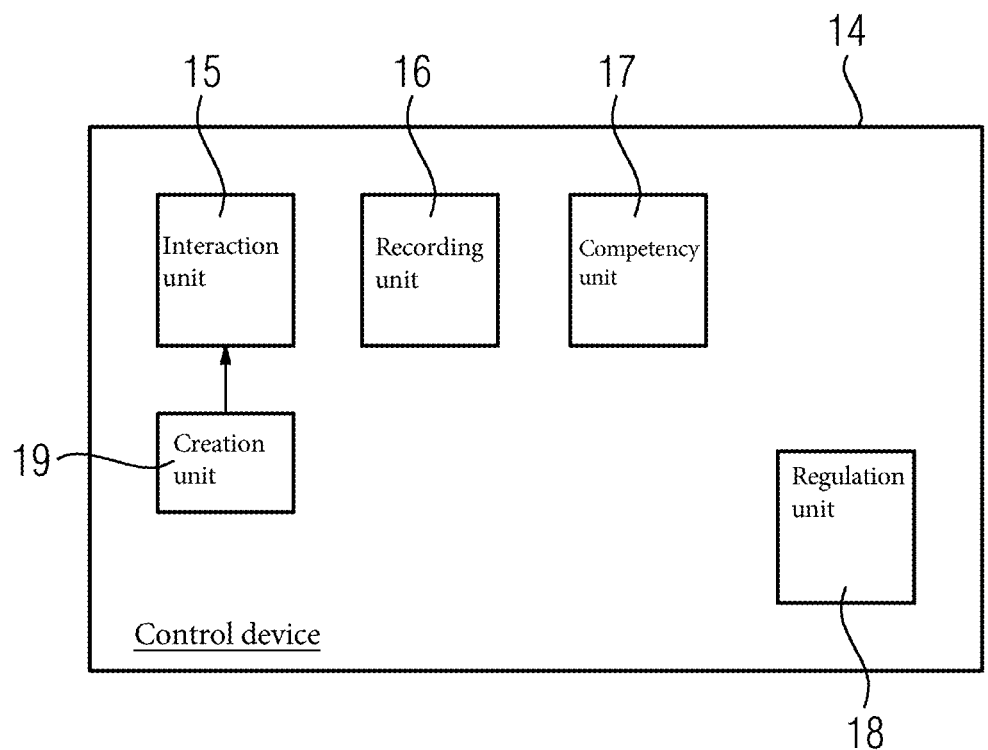

DETERMINING A COMPETENCY RELATIONSHIP, SETTING DOSE-RELATED RECORDING PARAMETER USING COMPETENCY RELATIONSHIP

The present patent document claims the benefit of German Patent Application No. 10 2018 215 958.0, filed Sep. 19, 2018, which is hereby incorporated by reference.

TECHNICAL FIELD

The disclosure relates to a method for determining at least one competency relationship to be used as a basis for selecting a dose-related recording parameter for an examination process, (e.g., the recording of a timed series of x-ray images as an x-ray image dataset of a patient at an x-ray device). The disclosure also relates to a method for the selection of at least one dose-related recording parameter for an examination process of a patient at an x-ray device, to an x-ray device, a computer program, and an electronically readable data medium.

BACKGROUND

X-ray devices are employed for a plurality of medical issues in processes for examining patients. Because the x-ray radiation used for imaging may be damaging for the patient, attempts are made to use as small a dose as possible. On the other hand, the visibility of clinically-relevant objects to be imaged by x-ray imaging, for example, of anatomical structures, and medical instruments in x-ray images depends on their contrast, meaning on the difference in the x-ray intensities of the x-ray radiation that passes through the object and the x-ray radiation that passes through the surrounding tissue. A further influencing factor is the image noise. In this case, the image quality may be described objectively by the Contrast to Noise Ratio (frequently abbreviated to CNR below). For a given x-ray image, the CNR is also a function of the spatial frequency, CNR(f) which shows that larger objects may be easier to see compared to smaller objects.

The so-called ALARA ("as low as reasonably achievable") principle is expediently to be employed for radiation protection in clinical practice. Thus, as little x-ray radiation as possible may be employed so that the corresponding examination processes still run successfully however. Because x-ray images that have been recorded with a lower x-ray dose for the patient exhibit a lower CNR, the ALARA principle implies the recording of x-ray images in which the relevant objects lie only slightly above the threshold of visibility.

It is problematic here that clinical practice does not allow any clear definition of a CNR threshold that is meaningful for all examination processes. Quite the opposite, there is a large transition area between a "comfort zone" and the point at which, because of the low CNR, the relevant objects are actually no longer visible. Comfort zone is to be understood here as x-ray images with a high CNR and correspondingly clearly visible objects being present. In this transition area, a reduction of the CNR leads to the following effects: (a) Increased time for interpretation/evaluation of the images on the part of the user, which in fluoroscopy leads to extended fluoroscopy times for example; (b) Increased risk of a misinterpretation (and thus possibly also of incorrect treatments); and (c) Increased mental stress because of a higher level of concentration needed.

In this case, it is important to note that the higher risk of misinterpretation of x-ray images with low CNR is unconsciously compensated for by the user, in that more time (or more attention) is devoted to the evaluation of the x-ray images, in that they are "inspected more carefully". Therefore, below a specific threshold, a further reduction of the CNR leads to a lengthening of the examination time for the recording of timed series of x-ray images, in particular the fluoroscopy, so that the cumulative irradiation of the patient also increases.

In respect of the problem of the choice of optimum image properties, e.g., recording parameters, in particular the CNR, approaches to solutions have become known at best in the prior art. Thus, it has been proposed that so-called fixed organ programs be specified, of which the CNR has been defined empirically as a result of feedback from users. This feedback is influenced by a plurality of factors however and is therefore not precise. Also proposed have been prolonged attempts at quality improvement, mostly a long time after an x-ray device has been installed.

SUMMARY AND DESCRIPTION

The scope of the present disclosure is defined solely by the appended claims and is not affected to any degree by the statements within this summary. The present embodiments may obviate one or more of the drawbacks or limitations in the related art.

The underlying object of the disclosure is to specify an improved basis for selection of recording parameters of an x-ray device for reducing the dose given to a patient.

This object is achieved by the method, the x-ray device, the computer program, and the electronically-readable data medium described herein.

Accordingly, a method for determining at least one competency relationship, to be used as a basis for selection of a dose-related recording parameter for an examination process, in particular, the recording of a timed series of x-ray images as an x-ray image dataset, of a patient at an x-ray device, between at least one user-specific or user group-specific competency value describing a user competency in respect of the evaluation of recorded x-ray images and at least the at least one recording parameter has the following acts for the user or for at least one user of the group: a number of x-ray image datasets corresponding to different recording parameters and/or having different image contents described by image content parameters are displayed to the user on a display facility; for each x-ray image dataset at least one measured value describing the competency value is recorded as a result of an interaction of the user with an operating device assigned to the display facility; and on the basis of the measured values, the competency relationship describing the recording parameter-dependent competency value is determined.

It is thus proposed, for at least a few aspects which relate to the competency of a user or of a user group to evaluate x-ray images of specific properties, to obtain quantitative competency relationships, in order to be able to discover improved recording parameters to be selected, in particular within the framework of an automatic dose monitoring. In other words, such competency relationships, in particular within the framework of the recording of timed series of x-ray images, (e.g., of fluoroscopy), allow settings of the x-ray device to be discovered that may again greatly reduce the dose for the patient compared to previously used "safety values", thus in particular allow the x-ray images to be recorded precisely tailored to the user-specific capabilities in such a way that on the one hand a reliable diagnosis by a user is possible, but on the other hand the dose for the patient is kept as low as possible, which corresponds to an improved implementation of the ALARA principle described above.

In this case, the term recording parameter is to be understood as having a wide interpretation within the framework of the present disclosure. Before an examination process, many operating devices also provide the opportunity to describe the examination process in relatively abstract terms, in order to derive herefrom suitable actual recording parameters to be used for the activation of components of the x-ray device. In other words, the user no longer absolutely has to enter directly values such as tube voltage, filters used and the like, but may enter examination targets, in particular target objects, their size, a desired contrast-to-noise ratio (CNR) and the like, from which the further recording parameters actually used for activation may be derived by a control device of the x-ray device. As an example of this, in a fluoroscopy as an examination process, for which the present disclosure may be used to particular advantage, a speed of movement to be expected of the relevant object to be observed may be specified, from which in its turn a suitable frame rate may be derived as a recording parameter. In such cases, x-ray devices have already been proposed, for which as recording parameters able to be specified by a user and/or as an intermediate act of an automatic dose process, the CNR itself is used as a recording parameter.

If in such an exemplary embodiment the quantitative dependence of the competency values on in particular at least the CNR values is known, it is thus possible, as will be explained in greater detail below, to discover especially advantageous values for this CNR and thus also for further recording parameters actually used for activation of the components of the x-ray device. This also applies to further conceivable recording parameters, for example a frame rate or the like.

In order to be able to establish such quantitative competency relationships, an automated learning process may be carried out for the user or for a group of users, in that the user reacts to x-ray datasets displayed to them on a display facility, (for example, a monitor of the x-ray device), and these reactions are recorded as measured values. In this way, an image-based measurement process for the user competency is implemented. Because the x-ray datasets are selected in this case so that they cover different values of the at least one recording parameter, measured values are thus available for different values of the at least one recording parameter, so that, through the appropriate evaluation, competency relationships may be discovered.

In this case, the term x-ray image dataset is also to be understood in a wide context. The x-ray datasets to be displayed may include actually recorded x-ray datasets of an x-ray device, but it is also conceivable to obtain x-ray datasets with the desired properties, (e.g., the desired recording parameters and/or image content parameters), by simulation to synthetically establish the datasets. In such cases, once again x-ray datasets actually recorded may serve as the basis for such simulated x-ray datasets.

In this case, it is important that different values of the recording parameters are covered by the x-ray datasets and, in particular, if the at least one competency relationship is to be determined for different applications/classes of examination processes, also to provide different constellations relating to the image content, in particular, of the target object. In this case, the reactions of the user are captured via an operating device, wherein the display facility may be embodied at least partly as a touch screen and be used as an operating device, through which an especially intuitive option for acquisition of the measured values is provided, which is characterized by few additional intellectual intermediate acts on the part of the user. In this case, the measured values may correspond at least in part to an entry of the user, but that it is also possible to take account of the circumstances of the input, for example, a time of the input, if a period of time for assessing the x-ray image dataset is to be queried as the competency value.

Because measured values for different recording parameters and image content parameters are present, the corresponding competency relationships that are desired are able to be determined. The competency relationships may be determined in a different form, wherein, e.g., a quantitative, functional competency relationship is defined. Look-up tables and the like are also conceivable however.

It is made possible by the disclosure to optimize x-ray parameters individually based on an image-oriented measurement process so that minimal patient dose is achieved for a specific user/a specific user group.

Embodiments of the present disclosure may make provision for a contrast-to-noise ratio (CNR) and/or a frame rate in a timed series of x-ray images and/or a recording parameter relating to the spatial resolution competency, in particular, in respect of a spatial frequency defined by a size of a target object and/or an object parameter describing image content parameters of at least one target object shown in the x-ray image dataset, in particular a medical instrument, such as at least one extent of the target object and/or a target object type to be used as recording parameters, and/or for anatomical noise to be used as a further variation parameter of the different x-ray datasets. Anatomical noise may be employed in this case for example as a density of anatomy surrounding the target object. The anatomical noise thus describes all x-ray signals deriving from the anatomy of a patient, but which are less relevant for the actual imaging task, thus for the examination process. In particular, when the examination process is fluoroscopy, a medical instrument may be used as target object, because this corresponds to the primary application, for example, in what are known as roadmap procedures.

In this case, not all recording parameters, as a function of which the competency value is described by the competency relationship, necessarily have to correspond to the at least one recording parameter ultimately to be selected (e.g., automatically) for a concrete examination process. In particular, the frame rate may already be defined based on pre-specified information describing the examination process, and is thus predetermined, and yet may not have an insignificant effect on the competency value, (for example, as regards the temporal integration of the human eye), which may achieve a temporal smoothing in fluoroscopy in respect of noise, which is in a direct relationship with the frame rate. Thus, the dependence of the competency value on such recording parameters exists and is thus also expediently to be known, even when these recording parameters are not able to be freely adapted with regard to the in particular automatic dose regulation.

As discussed above, an expedient development makes provision for the x-ray datasets for respective recording parameters and/or image content parameters defined to be selected at random from a permitted value group to be selected from predetermined x-ray datasets and/or to be created by a simulation. In this case, a creation of the x-ray datasets may be used, because the features relevant for the quantitative mapping of the competency, in particular as regards fluoroscopy as an examination process, are able to be simulated so that differences from actual, real x-ray images are barely perceptible. If, for example, a metallic guide wire is to be shown as a target object in an x-ray image dataset to be displayed, this may be simulated by a spline curve, which changes over time, possibly in accordance with a movement model. A target object temporally modulated in this way may be superimposed on a selected background, for example, a homogeneous background (e.g., white noise), on a background with anatomical noise and/or on a map of an actual or simulated mapped anatomy, for example based on x-ray datasets actually recorded with the x-ray device. Naturally, as well as a simple approach of this type, in which the target object is modeled via a simple model function and is superimposed on a selectable background, other approaches to synthetic creation of x-ray datasets are also conceivable, for example, by complete simulation of imaging processes, for example, on the basis of an actually recorded three-dimensional x-ray image dataset, from which x-ray images may be determined by forwards projection, for example, because the three-dimensional x-ray image dataset has been supplemented by a target object, for example a medical instrument. A plurality of options exists for creating x-ray datasets to be displayed for different recording parameters and/or image content parameters, without a large amount of x-ray datasets having to be held within the processing device carrying out the method.

Additionally, or alternatively, it is also possible to store real recorded x-ray datasets, to which specific recording parameters and/or image content parameters are assigned, in a memory device, for example in a database, and to retrieve them for display when required. For example, suitable, real recorded x-ray datasets may be selected by experts as being useful, and in particular provided after an anonymization.

Expediently x-ray datasets may be displayed for at least 2 to 10 different values of the recording parameters and/or for at least 2 to 5 different values of the image content parameters. The idea behind this embodiment is to keep the time for determining the competency relationship to a tolerable level for the user, so that in particular the overall time for recording the measured values is less than 20 minutes, or less than 15 minutes. To this end, it is expedient to select single, discrete values for the recording parameters and/or the image contents values, so that, when x-ray datasets are to be displayed for all combinations, the number of such sets is manageable. If, for example, around 200 x-ray datasets are assumed, for which processing lasts around three seconds on average, this results in 10 minutes for recording the measured values.

It is especially advantageous, when using a contrast-to-noise ratio as the recording parameter, to select the number of different values for the contrast-to-noise ratio as greater than the number of different values for other recording parameters, in particular five to nine values for the contrast-to-noise ratio and/or 2 to 4 values for other recording parameters and/or the image content parameters. If the signal-to-noise ratio, the frame rate, the target object size, (e.g., extent of the target object, correlated with the spatial frequency), and the target object type are considered, seven values for the contrast-to-noise ratio, three values for the frame rate, three values for the target object size and three target object types, (for example, stent, marker, and catheter endpoint), may be selected. When all combinations are considered, this produces a number of x-ray datasets of 7×3×3×3=189, thus for an average duration per x-ray dataset of 3 seconds, a test duration of 9.5 minutes.

While the x-ray datasets may be determined for determining the measured values based on all possible combinations of the values, it is also expedient to distribute the values to be used at random over the test duration.

In an embodiment, for recording the measured values, the user is set an evaluation task that may be the same for all x-ray datasets, (e.g., related to the target object), wherein user-side solution data is accepted by the operating device. In this case, the measured values may be produced from the solution data and/or the operating activity per se, in particular, from at least one point in time of the operating activity. It is also conceivable to deduce measured values from an operating activity not present. If an x-ray image dataset is displayed for a period of time that is longer than a time limit, without any operating activity having been determined, the user may move on to the next x-ray image dataset and at least one measurement value may be recorded that describes the fact that the set task has not been resolved.

In an advantageous embodiment, there may be provision for finding and/or identifying the target object to be set as the evaluation task. Such an embodiment is in particular expedient within the framework of the recording of series of x-ray images, in particular fluoroscopy. A fluoroscopy scene may then be ultimately shown as the x-ray image dataset with a specific frame rate as recording parameter. The primary task of the fluoroscopy is to find the target object in the images and where necessary to identify it. The portions of the image showing the target object are frequently referred to as the "signal". The user may then be presented with the evaluation task of finding and localizing the target object as quickly as possible. In this case the target object expediently involves a clinically relevant, possibly abstract signal, for example, relating to a marker, a guide wire of a specific size and/or another medical instrument. As explained, when a CNR is used as the recording parameter, the target object may then be shown with a corresponding CNR, for further use of a target object size as image content parameter, also with the corresponding value assigned to this x-ray image dataset. In this context of fluoroscopy as the examination process and the task definition described here, it is expedient to employ the artificially created, simulated x-ray datasets mentioned, for which the target object is ultimately superimposed on a selected background, dependent on the recording parameters and/or image content parameters.

In this case, more complex task definitions may also be implemented, for example, the display of a guide wire and/or marker and/or other medical instrument in a defined spatial relationship to an abstract blood vessel and the like.

In this case, it is further especially advantageous in this context for a time until the target object is found in the x-ray image dataset and/or an error rate to be used as competency values. This means that the selection contained in the solution data and also the period of time until this operating activity occurs are logged. An error rate may be derived from the solution data, because the correct solution is naturally known. The discovery time may be derived directly from the period of time that the user has needed to find the solution. An error is logged whenever the solution data is incorrect or when the task is not resolved within a predetermined time limit period.

In a concrete embodiment there may be provision for the displayed x-ray image of the x-ray image dataset to be divided up into a number of image areas and for the evaluation task to relate to finding the area of the image in which the target object is located. Image areas may thus be defined by superimposing a grid for example, wherein in particular, with an advantageous embodiment of the display facility as a touch screen, thus with integrated operating device, the user may mark the image area in which they believe they have found the target object as solution data by a simple input. For example, 4, 9 or 16 image areas may be chosen with basically square x-ray images of the x-ray dataset.

The x-ray datasets may be output in an order that is not specific, e.g., a randomized order in relation to the recording parameters and the image content parameters. This makes it possible to largely avoid patterns within the order of the presentation that may falsify the results. Additionally, or alternatively, at least two x-ray datasets may be output, for at least one set of the at least one recording parameter and/or the at least one image content parameter, wherein the measured values of these outputs will be statistically grouped together and/or evaluated for determining a time-dependent fatigue value during the overall display period of all x-ray datasets. Such a fatigue value may be considered for the evaluation, e.g., the establishment of the competency relationship. In this context it is thus proposed, for at least one set of recording parameters and image content parameters, meaning the same values for all recording parameters and all image content parameters, to output two x-ray datasets, in order to serve as a type of test sampling. In other words x-ray datasets with duplicated, already used values of the recording parameters and image content parameters may thus be inserted, in order on the one hand to obtain a distribution of the measured values for x-ray datasets with identical parameters, but on the other hand also to be able to identify a decreasing level of attentiveness, e.g., a level of fatigue.

In an expedient development, a number of image content-specific competency relationships may be determined and/or at least one competency relationship describing an additional dependence of the competency value on at least one of the at least one image content parameters may be determined. With regard to the image content parameters, a number of ways of approaching them are thus basically conceivable, which may also be used in combination. On the one hand, it is possible to determine a number of competency relationships for different values of image content parameters, for example, for different classes of target object sizes, in particular medical instruments, and/or different classes of anatomical noise. Different competency relationships may also be determined for different types of target objects for example. Depending on the actual examination process and its pre-specified information, the correct competency relationships or relationships derived therefrom may then be employed.

It is also conceivable for the competency relationship to specify the competency value not only as a function of at least one of the at least one recording parameters, but in addition also as a function of at least one of the at least one image content parameters. Then ultimately a suitable competency relationship exists even for different image content parameters, which may be mapped to corresponding specification information for examination processes, which may continue to be used seamlessly.

It is also conceivable to view the image content parameters only as basic variations and to employ them for averaging the competency over different scenarios for the same recording parameters.

The disclosure further relates to a method for selecting at least one dose-related recording parameter for an examination process of a patient at an x-ray device, wherein a competency relationship determined in accordance with what has been described above, which links the competency value used with at least the at least one recording parameter to be selected, is used for determining a dose minimization value for the recording parameters for the examination process, taking into account the competency.

The competency relationship is thus used directly or indirectly to select a suitable value for a dose-related recording parameter in such a way that the purpose of the examination process continues to be fulfilled for the user or for a user of the user group, but on the other hand a dose load on the patient at the x-ray device that is as low as possible is given, taking into account the competency of the user or of a user of the user group.

In this context, the capabilities may vary markedly between different users, depending on their experience, powers of observation, working conditions, and peculiarities of the environment. Therefore, the proposed methods also aim to match the recording parameters of an x-ray device to a specific user or to a group of users. At the same time, it is expedient already to provide both methods at the same x-ray device, which means that determining the competency relationship is already also delivered as a part of the product software of the x-ray device, because in this way a user-specific optimization of the automatic dose regulation of an x-ray device may take place entirely at the x-ray device, in that the subjective competency is quantified by the competency relationship.

This also means that the method described here for selecting a value of at least one dose-related recording parameter for an examination process of a patient at the x-ray device may be carried out within the framework of an automatic dose regulation, thus suitable values of the at least one recording parameter may be selected and set without the intervention of a user. To this end the x-ray device may in particular have an automatic dose regulation system or its control device may have an automatic dose regulation unit.

During the determination of the recording parameter to be selected, at least one item of default information describing the examination process, such as an image content parameter, (e.g., an object parameter), may be taken into account and/or the recording parameters determined in the dose minimization may be modified in respect of the thickness of the patient to be irradiated. Default information may be determined based on the input of a user, but also at least partly retrieved automatically for example from an information system, in particular a radiology information system. Default information may be mapped to image content parameters, so that it is made possible to select a competency relationship assigned to the corresponding values for the image content parameters or to use the image content parameters that are derived from the default information in the competency relationship or in a relationship derived therefrom. It is further expedient if, during the in particular automatic dose regulation, the recording parameter determined in the dose minimization is modified in respect of a thickness of the patient to be irradiated. The dependence of doses to be used for different thickness to be irradiated on the patient is already known in the prior art however and thus does not have to be explained further here.

In an advantageous embodiment, there may be provision that, for dose minimization, an equation is formulated relating the dose to an at least one competency value and thus via the at least one competency relationship to at least the at least one recording parameter to be selected of which the minima are to be determined. This advantageously means that it is possible via the competency values to set up a formula that relates the dose that is to be minimized to the recording parameters and in particular to the at least one recording parameter to be selected. This will be explained in greater detail with reference to an example of fluoroscopy, e.g., the recording of a timed sequence of x-ray images in the examination process.

Thus, for the planned recording of a timed series of x-ray images in the examination process and a discovery time, as described, the dose as a basic dose for a single x-ray image multiplied by the frame rate and the discovery time may be employed as the competency value. In this case, it also applies in a further embodiment that for a constant thickness of the patient the basic dose may also be employed in the form of a recording parameter, for example, as proportional to the square of the CNR. If the frame rate and the CNR have now been selected in any event as recording parameters in the determination of the competency relationship, an equation is produced in which the dose is only present as a function of these recording parameters, namely frame rate and CNR. Here, it is possible to discover the suitable minima for the at least one recording parameter to be selected, in particular the CNR.

If an error rate is also determined as the competency value, at least partly in the dose minimization one minus the error rate, where necessary with a descriptive factor additionally needed, the error rate may be inserted as a further factor, wherein this may also be iterated when taking account of consequent errors, so that a polynomial series may be produced. In this case, there may be provision for the at least one further factor only to be inserted if, for a resulting selection parameter to be selected, an error rate exceeding a threshold value is displayed as a result of the corresponding competency relationship.

In this context of the recording of a timed series of x-ray images, in particular of fluoroscopy, a contrast-to-noise ratio may be chosen as recording parameter to be selected, wherein the frame rate as further recording parameter is a fixed selection in particular on the basis of the default information. This means that while the frame rate may be selected as fixed for the purpose on the basis of the default information, the contrast-to-noise ratio represents a free parameter, which may be selected according to the competency of the user or the user group so that a dose load on the patient that is as small as possible is produced, but the purpose of the examination process is still reliably fulfilled. In this case, whenever a clinical indication for a specific frame rate is not given, an optimum for the rate may naturally also be found as a result of the competency relationship.

The dose minimization with the aid of the competency relationship may be started as an optimization method, in particular for more complex relationships that are produced. In simpler cases, it may also be entirely possible, for numerical or analytical discovery of the minima of the equation, to formulate a selection relationship. In other words, there may be provision for a selection relationship linking the optimal recording parameters to be selected with at least one further recording parameter and/or an image content parameter and/or an item of default information to be determined and be used for selection of the value of the recording parameter to be selected. This is useful, in particular, when the minima are able to be determined analytically or a function with an outstanding fit is found from analytically determinable minima.

Additionally, it is conceivable within the framework of the method described to employ methods of artificial intelligence. These are particularly suited to discovering correlations, which in particular involve the competency relationship. Thus the competency relationship, where necessary also the selection relationship, may include an artificial intelligence algorithm, wherein the ultimate determination of the competency process, e.g., the parameterization of the artificial intelligence algorithm, may then take place within the framework of machine learning, for example by deep learning or similar techniques.

An initial dose and/or a skin dose of the patient may be used as the dose to be minimized within the framework of the present disclosure. A dose study recently carried out by the applicant has indicated that a suitable strategy for reducing the patient dose is to significantly reduce the patient's skin dose. Such a reduction of the skin dose may lead to a lower image quality, which however in turn may lead to greatly extended fluoroscopy times during the fluoroscopy as examination process. However, the reduced initial patient dose per frame may compensate for the longer fluoroscopy time and thus lead to a reduction in the cumulative exposure of the patient to radiation. This result shows the necessity of the development of a method undertaken within the framework of the disclosure, which quantifies the balance between the image quality, the radiation load per frame and the fluoroscopy time, in order to realize the ALARA principle.

Thus, the skin dose as organ dose (the skin as an organ) may be seen as a critical variable. The reason for this is that stochastic damage, which plays a greater role in other organs, by contrast to deterministic damage, only occurs after relatively large temporal latency. Because the skin dose cannot be measured directly a number of methods have already been proposed for using the more or less proportional reference values as the point of reference.

In this case, the present disclosure is not only able to be usefully applied to fluoroscopic recordings, but may also be applied to radiography applications. While the emphasis with fluoroscopy is on the aforementioned discovery time, with radiography, in particular for setting up a corresponding equation, the emphasis may be placed far more on the error rate.

However, precisely in respect of the recording of timed series of x-ray images, in particular fluoroscopy, as already indicated it is entirely possible and sensible to employ the described method for also discovering optimal values for the at least one recording parameter to be selected dynamically during the examination process, in particular within the framework of a dynamic automatic dose regulation. Thus, there may be provision for the selection for dynamic adaptation to be made during the recording of a timed series of x-ray images in the examination process. For example, there may then also be analysis during the examination process as to how strong the anatomical noise currently is, in particular for example with a roadmap procedure, wherein then, when the anatomical noise was entered as an image content parameter into the competency relationship, a corresponding optimization of the values of the recording parameter may be adjusted to the anatomical noise. This applies in a similar way for other image content parameters and/or recording parameters that change during the examination process, the latter, for example, for a frame rate dynamically adapting itself during the examination process.

In summary, the present disclosure provides an improved way of supporting the implementation of the ALARA principle explained at the outset, in order to reduce the x-ray radiation to which the patient is exposed. This allows automatic dose regulations already present (REC—radiation exposure control) in x-ray devices to be expanded and improved. By contrast with the prior art, an automatic dose regulation based on the competency relationship may for the first time produce user-specific x-ray images, which are adapted in relation to an objective image recording parameter, in particular in relation to the contrast-to-noise ratio. If this option is employed as a significant advantage compared to previous dose regulation systems, the proposed methods, based on measured data, the measured values and exact mathematical models, allow an objective parameterization of the automatic dose regulation systems in order to create x-ray images that have exactly defined optimal image quality properties, configured to specific users, in particular optimal CNR values. In this way, the lowest patient doses may be obtained for each specific user. Because the radiation load for the patient is a significant factor for users, in particular, for the decision as to whether new x-ray devices are to be procured, the process described here may also lead to a particular commercial advantage.

As well as relating to the method described, the present disclosure also relates to an x-ray device having a control device embodied for carrying out the method disclosed herein. Everything that has been stated with regard to the method may be transferred analogously to the x-ray device, with which the advantages likewise already stated may thus also be obtained. In particular the acquisition of the user-specific or user-group-specific competency relationship may thus be performed at the x-ray device itself, meaning that said device has the appropriate equipment for determining the competency relationship itself and thus also for providing it to the x-ray device, in particular for an automatic dose regulation unit of the control device. This means that the x-ray device is delivered with the direct functionality for recording the necessary data for a user- or user-group-related further reduction of the patient dose and employing it subsequently.

The control device in this case may have at least one processor and at least one memory. Functional units may further be realized within the control device for different portions of the method as software and/or hardware. For example, the control device may have an interaction unit, which is responsible for the display of the x-ray datasets on the display facility and the provision of the facility for interacting via the operating device. A recording unit may record the measured values from or within the framework of the operating activity. An evaluation unit may determine the competency relationship on the basis of the measured values. As already mentioned, an automatic dose regulation unit may use the competency relationship or a relationship derived herefrom, in particular the selection relationship, in order to determine and set accordingly corresponding values for the at least one dose-related recording parameter to be selected, in particular the CNR.

A computer program is able to be loaded directly into a memory of a processing device, in particular a control device of an x-ray device for example, and has program code for carrying out the acts of the method when the computer program is executed in the processing device. The computer program may be stored on an electronically-readable data medium, which thus includes electronically-readable control information stored thereon, which includes at least one computer program and is embodied in such a way that, when the data medium is used in a processing device, in particular a control device of an x-ray device, it carries out the method.

The data medium may in particular involve a non-transient data medium, for example a CD-ROM.

BRIEF DESCRIPTION OF THE DRAWINGS

Further advantages and details of the present disclosure emerge from the exemplary embodiments described below and also with reference to the drawing. In the figures:

FIG. 5 depicts the functional layout of an example of a control device of the x-ray device as depicted in FIG. 4.

DETAILED DESCRIPTION

Figure 1:
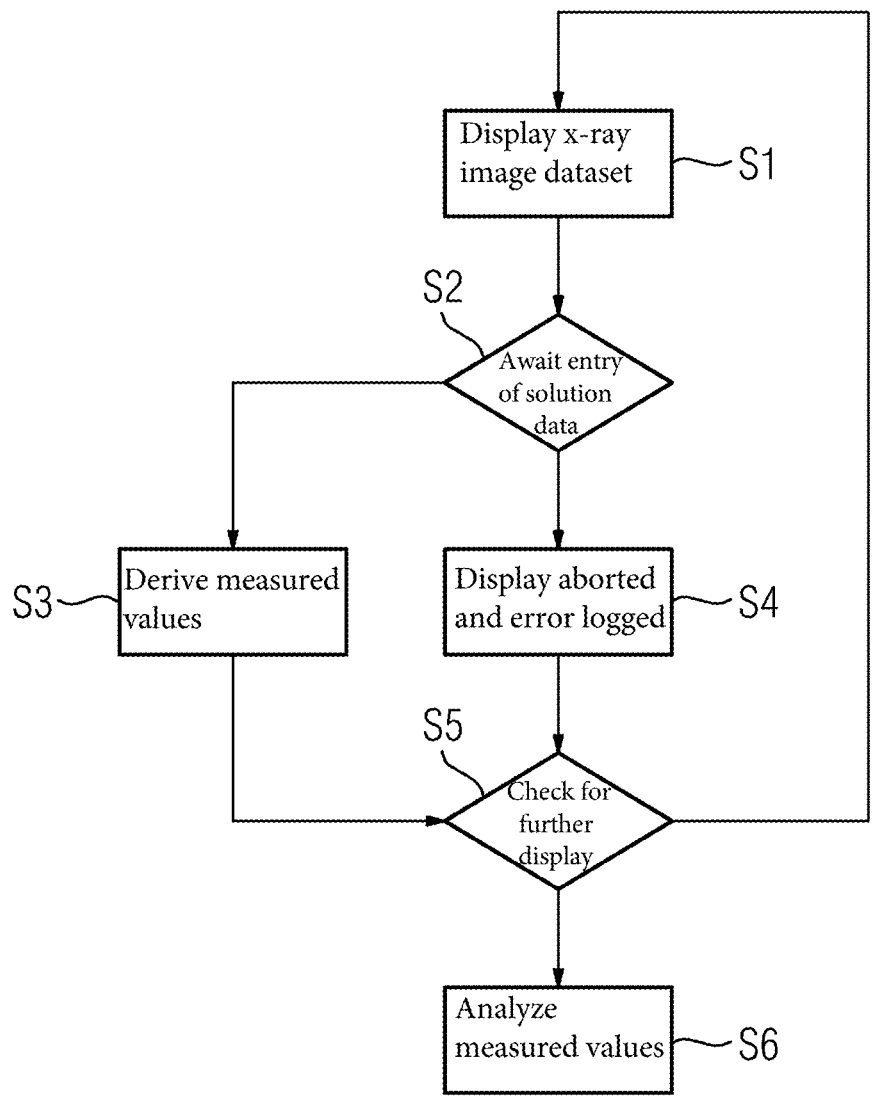
FIG. 1 depicts a flowchart of an example of a method for determining a competency relationship.

FIG. 1 depicts a flowchart of a concrete exemplary embodiment of a method for determining competency relationships, which may relate competency values to recording parameters and image content parameters or may determine them image-content-parameter-specifically in relation to the image content parameters. In this case, in the present example, fluoroscopy is considered as the examination process at which the dose reduction ultimately to be carried out is aimed, so that expediently the frame rate and the contrast-to-noise ratio (CNR) are employed as recording parameters. In this case, relationships between the CNR and further recording parameters, for example, tube voltages and the like actually used for activation of components of the x-ray device, are already known.

In this case, the described method for a user (or also a user of a group of users of similar competency) is carried out at the x-ray device itself, wherein a touch screen is employed as display facility with an integrated operating device. The recording of measured values for determining the competency relationships in this case is carried out in the present example in a "test" lasting for around 10 minutes for the user at the touch screen, which also serves to display current x-ray images of the fluoroscopy during an examination process of a patient. As an alternative, another visual display monitor may also be used in addition or as an alternative; other operating devices external to the display facility are of course also conceivable.

If the "test" is started for a user at the x-ray device, values of the recording parameters and the image content parameters are selected, for which simulated, thus computed, x-ray datasets are to be shown. X-ray datasets are to be understood in this case in the present example as series of x-ray images, which show at least one relevant target object, to be traced, for example, as is possible with fluoroscopy. Synthetic creation of such fluoroscopic x-ray images may take place for example by a mathematical model of the target object, in particular a medical instrument, being superimposed on a noise background. For example, a homogeneous background (e.g., white noise) and/or a predetermined strong anatomical noise may be employed as the background. A spline function changing over time according to a movement model is given as an example for a mathematical model of a guide wire. X-ray data actually recorded may of course also be included in such x-ray datasets to be created or may be used as a basis for such datasets.

While the CNR and the frame rate may be used as recording parameters, as already described, in the present example an object variable that is linked to the required spatial resolution, e.g., spatial frequency, and a target object type, for example catheter, marker, guide wire, . . . , may be used as image content parameters that describe the target object, e.g., object parameters. Included optionally as a further image content parameter is a variation parameter specifying the strength of anatomical noise.

The basic idea is now, for specific value tuples of values the recording parameters and of the image content parameters, to display x-ray datasets and to provide the user in this context with an evaluation task relating to the target object, in this case localization of the target object in one of many areas of the image, for example quadrants. To do this, in act S1, an x-ray image dataset is thus shown on the display facility as a fluoroscopy scene with the correspondingly assigned frame rate and the corresponding SNR.

Figure 2:
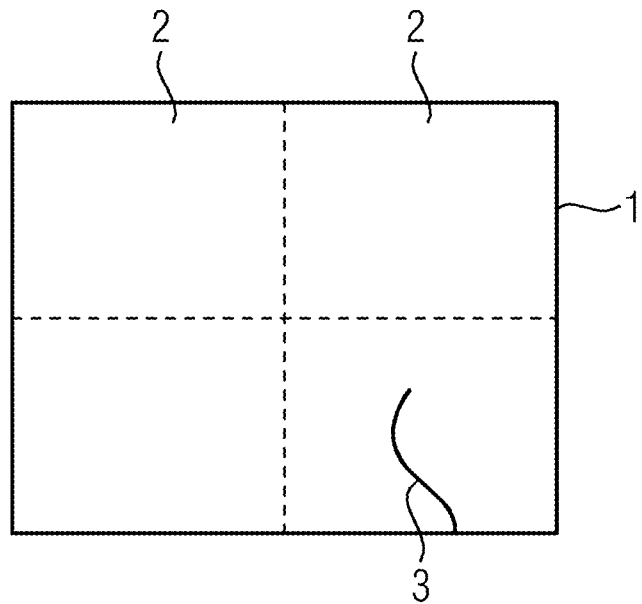
FIG. 2 depicts an example of a possible interaction concept for the method in accordance with FIG. 1.

As depicted in FIG. 2, by way of example, the entire x-ray image 1 shown may be divided into four image areas 2, wherein in one of these image areas 2 the "signal" of the target object 3 with the current SNR to be tested is contained.

In act S2, again cf. FIG. 1, the method now waits for the entry of solution data for the evaluation task posed via the operating device, until a predetermined time limit is reached. The solution data requires just one user input, namely a specification of the corresponding image area 2 on the basis of the evaluation task that the target object 3 be found and localized in one of the image areas 2. If there is an operating action, measured values are derived from the corresponding solution data and also the time of the operating action, here the time of the input of the solution data during the display of the x-ray image dataset and the correctness of the solution data. If the solution is not correct, an error is logged. This occurs in act S3.

If the period time limit is reached without an operating action, the display of the x-ray image dataset is aborted and in act S4, as measured values, the time until there is an operating action is set to a high value, for example the period time limit, and an error is likewise logged.

In this case, it may be assumed in the fluoroscopy example that on average the target object 3 may be found within 3 seconds in an x-ray image 1, e.g., a fluoroscopy scene. Therefore, the period time limit may be set as 5 seconds for example.

A check is then made in act S5 as to whether further x-ray datasets are to be displayed. If yes, the method continues again with act S1 and the next x-ray image dataset as well as the same evaluation task, if no, the method continues with act S6.

As already mentioned, a value tuple is assigned to each x-ray image dataset with a respective value for each recording parameter and a respective value for each image content parameter, thus in the present example for the CNR, the frame rate, the target object size and the target object type. Overall, there may be provision for using a specific number of values predetermined or selected at random for each of these parameters in all permutations, wherein, e.g., for the central variable, namely CNR, more individual values are covered than for the other parameters. In this concrete exemplary embodiment seven different values are employed for the CNR, three different values for the frame rate, three different values for the target object size and three different values for the target object type, for example stent, marker and catheter tip. Optionally, as already mentioned, values for the density of the anatomical structures, e.g., the anatomical noise, may also be employed, for example likewise three values.

The x-ray datasets are based on all possible combinations of these defined values, distributed at random during the duration of the test described here. In this case check x-ray datasets with repeating value combinations may expediently be inserted, in order to obtain the distribution of the measured values for this value combination or this value tuple, thus to make possible a statistical evaluation; at the same time however a fatigue value based on such repeated value combinations may also be monitored, for example, a falling level of a attention over the test, which may then likewise be taken into account in the evaluation in act S6 in accordance with FIG. 1.

In the present example, the number of value combinations, e.g., value tuples, which are produced without taking account of the anatomical noise, is 7×3×3×3, (i.e., 189), whereby a total test duration of 9.5 minutes is produced for an average duration per x-ray image dataset of 3 seconds; if repeated value combinations are employed, the duration of the test may be restricted to 10 minutes or slightly more.

In act S6, there then follows a statistical analysis of the measured values, in order to obtain the competency relationships. In the present example, two competency values are considered, namely on the one hand the discovery time, e.g., to time it takes to come to a decision. The second competency value is the probability of an error. The respective competency relationships are determined separately in each case for the different target object types in this case, so that ultimately the frame rate is labeled R and the object size, because of its close relationship with the spatial frequency, is produced as f, as competency relationships T (CNR, R, f) for the discovery time and E (CNR, R, f) for the error probability.

These competency relationships may now be used for an examination process to discover an optimal dose-minimizing CNR to be used, taking into account the competency of the user, because the starting point is the assumption that, because of the clinical requirements, the frame rate is already to be defined as a fixed value. Thus, the method operates with this predetermined frame rate.

Figure 3:
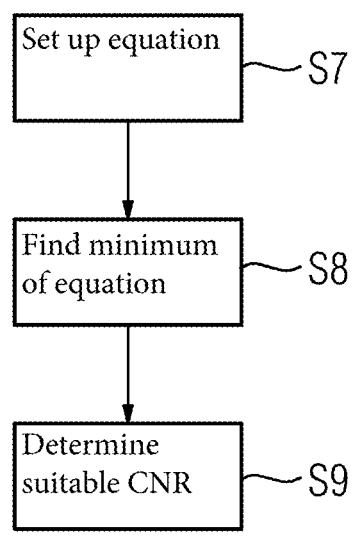
FIG. 3 depicts a flowchart of an example for selecting a value for a dose-related recording parameter.

FIG. 3 depicts an example of a flowchart for such a selection of a value for a dose-related recording parameter, here the CNR.

In this case an equation is set up in act S7, which creates a relationship between the patient dose and the competency value and thus via the competency relationship with the recording parameters, wherein the assumption is also made below that the target object size for the examination process belongs to the default parameters.

In act S8, a minimum of this equation may be found, which describes the optimum CNR that is dose-reducing and yet still allows the purpose of the examination. This is then selected in act S9 and applied accordingly, e.g., set up in the examination process, wherein the dynamic adaptation may take place during the examination process, actually also a fluoroscopy. In this case, it is conceivable to carry out the acts S7 and S8 beforehand for general frame rates and target object rates and each target object type, in order to obtain selection relationships of a general type, from which then, in act S9, the suitable CNR may be determined for the actual examination process.

An example of the process that may be used in the case of fluoroscopy with a predetermined frame rate and predetermined target object size is explained below in detail. Within the framework of the dose regulation described here, there may also be an adaptation to the thickness of the patient, which may be superimposed however and is basically already known.

The initial patient dose that is required to record a frame, e.g., an individual x-ray image, is used as the patient dose here. This is dependent on the patient thickness and the CNR and may be written as D (thickness, CNR). Thus, the initial patient dose that is required to make a correct clinical decision may be written as:

$$D_{decision} = D(\text{thickness}, CNR) \cdot R \cdot T(CNR, R, f) \quad (1)$$

For a given thickness of the patient to be irradiated the initial dose per frame D(thickness, CNR) is proportional to the square of the CNR, so that it may be written as follows:

$$D_{decision} \approx CNR^2 \cdot R \cdot T(CNR, R, f) \quad (2)$$

In order to discover the value of the CNR, which corresponds to the minimum radiation load for the patient and with which at the same time a correct clinical decision may be made, the minimum of the function (2) is found. Therefore, the following equation is solved analytically, if possible, or numerically:

$$\frac{\partial D_{decision}}{\partial CNR} = \quad (3)$$
$$2 \cdot CNR \cdot R \cdot T(CNR, R, f) + CNR^2 \cdot R \cdot \frac{\partial T(CNR, R, f)}{\partial CNR} = 0$$

$$2 \cdot T(CNR, R, f) + CNR \cdot \frac{\partial T(CNR, R, f)}{\partial CNR} = 0 \quad (4)$$

The solution of equation (4) is dependent on the frame rate R and the spatial frequency f, CNR_optimum (R, f). This CNR shows the working conditions under which on the one hand the smallest possible radiation dose may be administered to the patient, but on the other hand a sensible clinical decision may be made. That means that operation is in accordance with the ALARA principle.

When the solution of equation (4) lies in a CNR range with a high probability of error E (CNR, R, f), the radiation dose model of the equation (1) or (2) may be modified to take account of the measured error rate. However, the following radiation dose model, taking account of both T and also E, may also be employed from the outset.

An example of such a model for the initial patient dose, which also takes account of an error that would require the examination process to be repeated at least once, is given by equation (5).

$$D_{decision} = D(\text{thickness}, CNR) \cdot R \cdot T(CNR, R, f) \cdot (1 + E(CNR, R, f)) \quad (5)$$

The possibly longer period of time that is needed to recognize and to correct the error may be included by a factor k>1, which leads to:

$$D_{decision} = D(\text{thickness}, CNR) \cdot R \cdot T(CNR, R, f) \cdot (1 + k \cdot E(CNR, R, f)) \quad (6)$$

The repetition of the examination process or of the evaluation may lead to secondary errors, which once again require additional correction. The secondary, tertiary and further errors and the corresponding time required may be taken into account by a sum:

$$D_{decision} = \quad (7)$$
$$D(\text{thickness}, CNR) \cdot R \cdot T(CNR, R, f) \cdot (1 + kE + (kE)^2 + (kE)^3 + \ldots)$$

$$D_{decision} = D(\text{thickness}, CNR) \cdot R \cdot T(CNR, R, f) \cdot \frac{1}{1 - k \cdot E(CNR, R, f)} \quad (8)$$

In this way, by using this model for the initial patient dose as first approximation through a renewed process for discovering the minima, the CNR setting may be found that leads to the lowest radiation load on the patient while fulfilling the purpose of the examination, in that the minimum of the function:

$$D_{decision} \approx \frac{CNR^2 \cdot R \cdot T(CNR, R, f)}{1 - k \cdot E(CNR, R, f)} \quad (9)$$

will be discovered. This optimal CNR is dependent on the frame rate R and the spatial frequency f, CNR_optimum (R, f).

Regardless of whether the procedure described is carried out individually for each case or a general selection relationship may be derived from an analytical or numerical solution of the equation (4) or (9), this dose regulation may take place automatically in an automatic dose regulation unit of a control device of the x-ray device, so that ultimately, default information regarding the examination procedure is entered, a target object type, a frame rate and a target object size are derived therefrom and then, using these parameters, an optimal CNR may be determined automatically. This may also take place dynamically, if one of the other recording parameters or one of the image content parameters changes during the examination procedure, for example, when an exchange of the medical instrument takes place, the anatomical noise adapts itself or the like.

Figure 4:
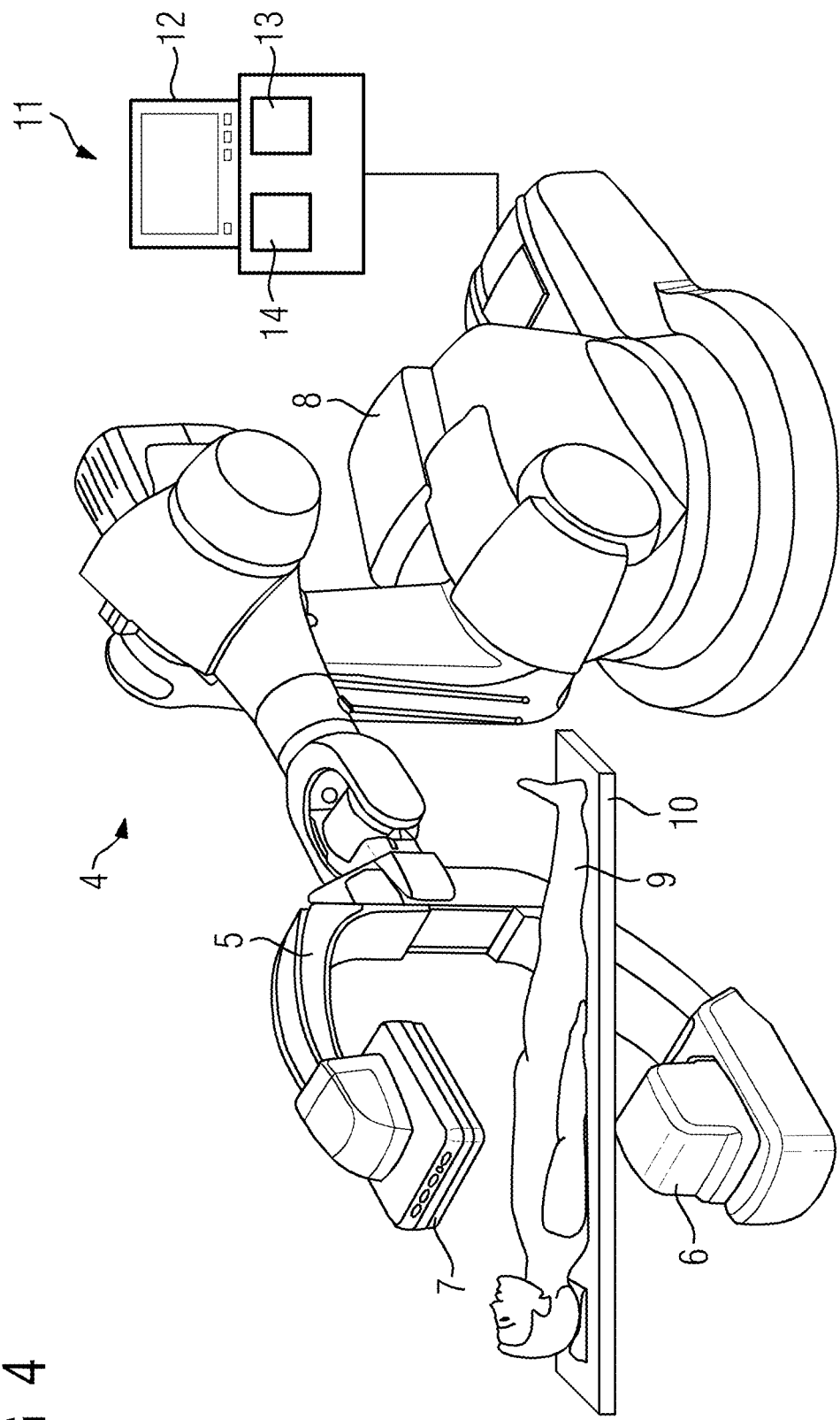
FIG. 4 depicts an example of an x-ray device.

FIG. 4 depicts a basic diagram of an x-ray device 4, which is embodied in the present example as an angiography device with a C-arm 5, on which an x-ray detector 6 and an x-ray emitter 7 are arranged opposite one another. The C-arm 5 is carried on a robot arm 8 in the present example, so that optimal angulations in relation to a patient 9 on a patient table 10 may be selected for an examination process.

The x-ray device 4 further has an interaction device 11, which as well as a display facility 12, in particular, a visual display monitor for recorded x-ray images, also includes an operating device 13. In other embodiments, the display facility or a display facility 12 may also be embodied as a touch screen, which may already contain the operating device or component 13 integrated within it.

The operation of the x-ray device 4 is started by a control device 14, which is also embodied for carrying out the method.

FIG. 5 depicts an example of a possible functional layout of the control device 14. To carry out the acts S1 to S6, the control device 14 may have an interaction unit 15 in this case, for example, which activates the display facility 12 for output of x-ray datasets and in particular monitors the operating device or component 13 for operating activities. In a recording unit 16, measured values may be recorded from the operating activity present or not present, wherein a competency unit 17 evaluates the measured values in conjunction with the parameters of the associated x-ray datasets, in order to obtain the competency relationships. The interaction unit 15 may be supplied by a creation unit 19 for creating simulated x-ray datasets, as described.

The control unit 14 further has an automatic dose regulation unit 18, which carries out the general dose regulation on a current patient and examination process, in the present example taking into consideration the competency relationships for better fulfillment of the ALARA principle. Naturally the automatic dose regulation unit 18 may include further functional subunits, in particular including a superimposed subunit for adapting recording parameters determined to the actual given patient thickness to be irradiated.

A method described herein may also be present in the form of a computer program, which implements the method on the control device 14 when it is executed on the control device 14. Likewise an electronically-readable data medium with electronically-readable control information stored thereon may be present, which includes at least one described computer program and is embodied in such a way that, when the data medium is used in the control device 14 of the x-ray device 4, it carries out a described method.

Overall the subject matter described here thus gives the opportunity to obtain relationships at the x-ray device 4 itself for optimal dose minimization at a patient 9 in a short test, which are then used within the x-ray device 4 itself for an automatic dose regulation, which allow a further reduction of the patient dose and are thus suitable for an improved fulfillment of the ALARA principle.

Although the disclosure has been illustrated and described in greater detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for determining a dose-related recording parameter for an examination process for a recording of a timed series of x-ray images as an x-ray image dataset of a patient at an x-ray device, the method comprising:
displaying, by a display device, a plurality of x-ray image datasets corresponding to different recording parameters and/or having different image contents described by image content parameters;
recording, by the x-ray device for each x-ray image dataset, at least one measured value describing a competency value based on an interaction of a user with an operating device assigned to the display device, wherein the competency value describes a user-specific or user group-specific user competency in respect of an evaluation of the timed series of x-ray images by the user;
automatically regulating, by a control device of the x-ray device, a radiation dose given to the patient during the examination process by determining a competency relationship describing a recording parameter-dependent competency value based on the measured values and determining a dose-minimizing value for the dose-related recording parameter for the examination process using the competency relationship; and
conducting, by the x-ray device, the examination process of the patient using the dose-minimizing value, wherein the radiation dose provides a reduced dose to the patient and generates user-specific or group-specific x-ray images in comparison to a similar examination process of the patient without a process of determining the competency relationship,
wherein the user is given a same evaluation task for all x-ray image datasets of the plurality of x-ray image datasets,
wherein the operating device receives user-side solution data from the user, and
wherein discovery of a target object is set as the evaluation task and/or a discovery time until the target object is discovered in the x-ray image dataset and/or an error rate are used as the competency value.

2. The method of claim 1, wherein one or more of a contrast-to-noise ratio for the timed series of x-ray images, a frame rate for the timed series of x-ray images, or a recording parameter relating to a spatial resolution competency is used as a recording parameter or object parameter describing at least one target object shown in the x-ray image dataset, or
wherein an anatomical noise is used as a variation parameter of the x-ray image dataset.

3. The method of claim 2, wherein the contrast-to-noise ratio is a function of a spatial frequency defined by a size of the target object.

4. The method of claim 2, wherein the target object is a medical instrument.

5. The method of claim 2, wherein at least one extent of the target object, a target object type, or a combination thereof is used as an image content parameter.

6. The method of claim 1, wherein the plurality of x-ray image datasets for the recording parameters and/or the image content parameters, defined in each case at random from a permitted group of values, are selected from predetermined x-ray image datasets and/or are created by a simulation.

7. The method of claim 1, wherein the plurality of x-ray image datasets for at least 2 to 10 different values of the recording parameters and/or for at least 2 to 5 different values of the image content parameters are displayed.

8. The method of claim 1, wherein an x-ray image of the plurality of x-ray image datasets is divided into a plurality of image areas, and
wherein the evaluation task relates to a discovery of an image area of the plurality of image areas in which the target object is located.

9. The method of claim 1, wherein the plurality of x-ray image datasets is output in a randomized order in relation to the recording parameters and the image content parameters, or, for at least one set of the recording parameters and/or the image content parameters, at least two x-ray image datasets of the plurality of x-ray image datasets are output, and
wherein the measured values of the output x-ray image datasets are statistically summarized and/or evaluated for determining a time-dependent fatigue value for an overall period during which all x-ray image datasets of the plurality of x-ray image datasets are displayed.

10. The method of claim 1, wherein a plurality of image-content-parameter-specific competency relationships is determined and/or at least one competency relationship is determined describing an additional dependency of the competency value on at least one image content parameter of the image content parameters.

11. The method of claim 1, wherein the recording of the at least one measured value comprises a machine learning process in which the user or a group of users react to x-ray datasets displayed on the display device and reactions of the user or the group of users are recorded as the at least one measured value.

12. A method for selection of at least one dose-related recording parameter for an examination process of a patient at an x-ray device, the method comprising:
  recording, by the x-ray device for each x-ray image dataset of a plurality of x-ray image datasets, at least one measured value describing a competency value based on an interaction of a user with an operating device assigned to a display device, wherein the competency value describes a user-specific or user group-specific user competency in respect of an evaluation of x-ray images by the user, and wherein the recording of the at least one measured value comprises a machine learning process in which the user or a group of users react to x-ray datasets displayed on the display device and reactions of the user or the group of users are recorded as the at least one measured value;
  automatically regulating, by a control device of the x-ray device, a radiation dose given to the patient during the examination process by: determining a competency relationship describing a recording parameter-dependent competency value based on the measured values, which links the competency value with at least one recording parameter of the at least one dose-related recording parameter to be selected; and determining a dose-minimizing value for the recording parameter for the examination process using the determined competency relationship; and
  conducting, by the x-ray device, the examination process of the patient using the dose-minimizing value.

13. The method of claim 12, wherein, for the determining of the dose-minimizing value for the recording parameter, the recording parameter determined is modified by the control device of the x-ray device in respect of a thickness of the patient to be irradiated.

14. The method of claim 13, wherein the recording parameter is an image content parameter or an object parameter.

15. The method of claim 12, wherein, in the determining of the dose-minimizing value, an equation setting a dose in relation to the competency value and via the competency relationship to at least the at least one recording parameter to be selected is formulated, of which minima are determined.

16. The method of claim 15, wherein a selection relationship linking optimal recording parameters to at least one further recording parameter and/or an image content parameter and/or an item of default information is determined and is used for the selection of the recording parameter.

17. The method of claim 12, wherein, for a recording of a timed series of x-ray images in the examination process, a dose as a basic dose multiplied by a frame rate for the timed series of x-ray images and a discovery time until a target object is discovered in an x-ray image dataset is formulated as the competency value.

18. The method of claim 17, wherein the competency value uses one minus an error rate as an additional factor.

19. The method of claim 12, wherein an initial dose or a skin dose of the patient is used as a dose.

20. The method of claim 12, wherein the selection is made for dynamic adaptation during the recording of a timed series of x-ray images in the examination process.

21. An x-ray device comprising:
  a control device configured to:
    display a plurality of x-ray image datasets corresponding to different recording parameters and/or having different image contents described by image content parameters;
    record, for each x-ray image dataset, at least one measured value describing a competency value based on an interaction of a user with an operating device, wherein the competency value describes a user-specific or user group-specific user competency in respect of an evaluation of recorded x-ray images by the user;
    automatically regulate a radiation dose given to a patient during an examination process of the patient by: determining a competency relationship to be used as a basis for selecting a dose-related recording parameter for the examination process for recording a timed series of x-ray images as an x-ray image dataset of the patient of the x-ray device, the competency relationship describing a recording parameter-dependent competency value based on the measured values and determining a dose-minimizing value for the dose-related recording parameter for the examination process using the competency relationship; and
    conduct the examination process of the patient using the dose-minimizing value, wherein the radiation dose provides a reduced dose to the patient and generates user-specific or group-specific x-ray images in comparison to a similar examination process of the patient without a process of determining the competency relationship.

* * * * *